(12) United States Patent
Minetoma (10) Patent No.: US 8,797,393 B2
(45) Date of Patent: Aug. 5, 2014

(54) ELECTRONIC ENDOSCOPE SYSTEM, PROCESSING APPARATUS FOR ELECTRONIC ENDOSCOPE, AND SIGNAL SEPARATION METHOD

(75) Inventor: Yasuhiro Minetoma, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 356 days.

(21) Appl. No.: 12/940,192

(22) Filed: Nov. 5, 2010

(65) Prior Publication Data

US 2011/0109734 A1    May 12, 2011

(30) Foreign Application Priority Data

Nov. 6, 2009  (JP) ................................ 2009-255161

(51) Int. Cl.
*H04N 3/10* (2006.01)
*H04N 5/225* (2006.01)

(52) U.S. Cl.
CPC .................................. *H04N 5/2256* (2013.01)
USPC ................................. 348/68; 348/45; 348/65

(58) Field of Classification Search
CPC ........................... A61B 1/0638; H04N 5/2256
USPC ............................................... 348/45, 65–78
See application file for complete search history.

(56) References Cited

U.S. PATENT DOCUMENTS

| 2003/0176768 | A1 | 9/2003 | Gono et al. | |
| 2008/0174701 | A1* | 7/2008 | Iketani et al. | 348/687 |
| 2008/0281207 | A1* | 11/2008 | Johnston | 600/476 |
| 2010/0030021 | A1* | 2/2010 | Minai et al. | 600/109 |

FOREIGN PATENT DOCUMENTS

| EP | 1 787 577 A1 | 5/2007 |
| JP | 2001-74555 A | 3/2001 |
| JP | 3559755 B2 | 9/2004 |
| WO | WO 2006/122390 A1 | 11/2006 |
| WO | WO 2008/136801 A1 | 11/2008 |

* cited by examiner

*Primary Examiner* — Christopher S Kelley
*Assistant Examiner* — Jonathan Messmore
(74) *Attorney, Agent, or Firm* — Birch, Stewart, Kolasch & Birch, LLP (57) ABSTRACT

Image capture is performed while broadband and narrow band light are simultaneously emitted to tissue site. B pixel sensing the narrow band light outputs a summed image signal having a brightness value of a B component of the broadband light and a brightness value of the narrow band light. G and R pixels, not sensing the narrow band light, output broadband image signals having brightness values of G and R components of the broadband light, respectively. Based on correlation information and the G component of the broadband light, the brightness value of the B component of the broadband light is obtained. The obtained brightness value is subtracted from the summed image signal to separate the brightness value of the narrow band light therefrom. A broadband image and a narrow band image are generated from the broadband image signals and the narrow band image signal, respectively.

9 Claims, 7 Drawing Sheets

ELECTRONIC ENDOSCOPE SYSTEM, PROCESSING APPARATUS FOR ELECTRONIC ENDOSCOPE, AND SIGNAL SEPARATION METHOD

FIELD OF THE INVENTION

The present invention relates to an electronic endoscope system for obtaining a broadband image and a narrow band image of a tissue site, a processing apparatus for an electronic endoscope, and a signal separation method.

BACKGROUND OF THE INVENTION

Recently, diagnoses and medical treatments using electronic endoscopes are commonly performed in the medical field. An electronic endoscope has a long insert section to be inserted into a patient's body cavity. The electronic endoscope incorporates an imaging section such as a CCD at its distal end. The electronic endoscope is connected to a light source apparatus. The light source apparatus delivers light to the electronic endoscope via a light guide such as an optical fiber. The electronic endoscope emits the light from its distal end to illuminate the body cavity. The imaging section at the distal end of the insert section captures an image of a tissue site in the body cavity while the body cavity is illuminated. The image is subjected to various processes in a processing apparatus connected to the electronic endoscope, and then displayed on a monitor. With the use of the electronic endoscope, a doctor can observe an image of the tissue site in the patient's body cavity real-time, which ensures accurate diagnosis.

The light source apparatus is a white light source, for example, a xenon lamp that emits white broadband light ranging from blue light to red light. An image (hereafter referred to as broadband image) captured with the illumination of the white broadband light shows the overall condition of the tissue site, for example, mucosa located on a surface of the tissue site, blood vessels inside the tissue, the shape and condition of the surface of the mucosa such as protrusion or depression, and the presence or absence of polyp.

In addition to the observation of the broadband image, observation with "special light", that is, the observation using a narrow band light source that emits narrow band light in a specific wavelength range is performed as disclosed in Japanese Patent No. 3559755 (corresponding to U.S. Patent Application Publication No. 2003/0176768), for example. Light penetrates deeper into the tissue site as its wavelength increases, namely, blue light, green light, and red light increase in penetration depth in this order. Using the difference in the penetration depth, the endoscope system of Japanese Patent No. 3559755 generates a narrow band image in which blood vessels at a specific depth (for example, at the surface or at the depths) are enhanced. For example, with the emission of blue narrow band light having a small penetration depth, a narrow band image is generated with enhanced surface blood vessels. With the emission of green narrow band light having the penetration depth larger than that of the blue narrow band light, a narrow band image is generated with enhanced blood vessels located at the depth deeper than the surface. Thus, the blood vessels at a specific depth are more clearly observed in the narrow band image than in the broadband image.

To perform a diagnosis, it is preferable to observe both the narrow band image with enhanced blood vessel regions and the broadband image showing the overall condition of the tissue site. The endoscope system disclosed in Japanese Patent No. 3559755 captures an image using a spectral filter having a first area and a second area. The first area allows the broadband light emitted from the white light source to pass through it. The second area only allows the narrow band light to pass through it. The filter allows the simultaneous display of both the narrow band image and the broadband image. Additionally, the endoscope system of Japanese Patent No. 3559755 is provided with a mechanical drive mechanism to move the spectral filter such that one of the first and second areas of the spectral filter is inserted into the optical path of the white light source. Operating the drive mechanism moves the spectral filter to switch between the broadband light and the narrow band light.

The image sensor such as a CCD used in the electronic endoscope outputs image signals at 30 fps (frames per second) or 60 fps. Because the apparatus disclosed in Japanese Patent No. 3559755 mechanically moves a spectral filter to switch between the narrow band light and the broadband light, there is a time lag between obtaining an image signal for generating the narrow band image and obtaining an image signal for generating the broad band image. As a result, due to the motion of patient's body and the insert section during the time lag, misregistration between the narrow band image and the broadband image occurs.

To prevent the misregistration, a method using an acousto-optic filter is devised as disclosed in Japanese Patent Laid-Open Publication No. 2001-074555. With the application of vibration, the acousto-optic filter separates the narrow band light in a specific wavelength range from the broadband light such as white light. The acousto-optic filter is placed in front of the image sensor, so the light passes through the acousto-optic filter before it reaches the image sensor. Thereby, the acousto-optic filter separates the narrow band light in the specific wavelength range from the broadband light. However, the acousto-optic filter is expensive and increases cost.

SUMMARY OF THE INVENTION

An object of the present invention is to provide an inexpensive electronic endoscope system for obtaining both the broadband image and the narrow band image without causing misregistration, a processing apparatus for an electronic endoscope, and a signal separation method.

The electronic endoscope system of the present invention includes an imaging section, an emission section, a signal obtaining section, a correlation information storage, and a signal separator. A blue pixel, a green pixel, and a red pixel are arranged the imaging section. The blue pixel senses blue light to generate a blue color signal. The green pixel senses green light to generate a green color signal. The red pixel senses red light to generate a red color signal. The emission section emits white broadband light and narrow band light to a tissue site in a body cavity. The tissue site includes a blood vessel. The white broadband light ranges from the blue light to the red light. The narrow band light is in a wavelength range sensed by only one or two of the three pixels. The signal obtaining section reads the color signals in time order from the imaging section and obtains a mixed image signal during emission of the broadband light and the narrow band light. The mixed image signal includes a broadband image signal corresponding to the broadband light and a narrow band image signal corresponding to the narrow band light. The correlation information storage stores correlation information between the at least one color signal generated without sensing the narrow band light and the one or two color signals generated by sensing the narrow band light from among the blue, green, and red color signals included in the broadband image signal.

The signal separator separates the mixed image signal into the broadband image signal and the narrow band image signal in consideration of the correlation information.

It is preferable that the electronic endoscope system further includes an electronic endoscope, a processing apparatus connected to the electronic endoscope, and a light source apparatus connected to the electronic endoscope. It is preferable that the electronic endoscope is provided with the emission section, the signal obtaining section, and the imaging section. It is preferable that the processing apparatus is provided with the correlation information storage and the signal separator. It is preferable that the light source apparatus is provided with a light source for generating the narrow band light. A part of the narrow band light passes through a fluorescent member provided in the endoscope. The fluorescent member converts a remainder of the narrow band light into the broadband light.

It is preferable that the signal separator executes a step for calculating a broadband image signal of the pixel sensing the narrow band light from a color signal of the pixel not sensing the narrow band light and the correlation information, and a step for subtracting the calculated broadband image signal from the mixed image signal to obtain the narrow band image signal.

It is preferable that the pixel sensing the narrow band light is the blue pixel. In this case, it is preferable that the narrow band light is in a wavelength range of 440±10 nm or 400±10 nm.

It is preferable that the pixel sensing the narrow band light is the blue pixel and the green pixel. In this case, it is preferable that the narrow band light is in a wavelength range of 470±10 nm.

It is preferable that the electronic endoscope system further includes a monitor for displaying a broadband image based on the broadband image signal and a narrow band image based on the narrow band image signal.

A processing apparatus, connected to an electronic endoscope, includes, a signal obtaining section, a correlation information storage, and a signal separator. The signal obtaining section reads the color signals in time order from the imaging section and obtains a mixed image signal during the emission of the broadband light and the narrow band light. The mixed image signal includes a broadband image signal corresponding to the broadband light and a narrow band image signal corresponding to the narrow band light. The correlation information storage stores correlation information between at least one color signal generated without sensing the narrow band light and one or two color signals generated by sensing the narrow band light from among the three signals included in the broadband image signal. The signal separator separates the mixed image signal into the broadband image signal and the narrow band image signal in consideration of the correlation information.

A signal separation method for separating an image signal of an electronic endoscope includes an emitting step, an obtaining step, a reading step, and a separating step. In the emitting step, white broadband light and narrow band light are emitted to a tissue site in a body cavity. The tissue site includes a blood vessel. The white broadband light ranges from the blue light to the red light. The narrow band light is in a wavelength range sensed by only one or two of the three pixels. In the obtaining step, an image of the tissue site is captured with the imaging section during emission of the broadband light and the narrow band light to obtain a mixed image signal. The mixed image signal includes a broadband image signal corresponding to the broadband light and a narrow band image signal corresponding to the narrow band light. In the reading step, correlation information is read from a correlation information storage. The correlation information represents a correlation between at least one color signal generated without sensing the narrow band light and one or two color signals generated by sensing the narrow band light from among the three color signals included in the broadband image signal. In the separating step, the mixed image signal is separated into the broadband image signal and the narrow band image signal in consideration of the correlation information.

According to the present invention, both the broadband image and the narrow band image are obtained without misregistration and without additional parts cost.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
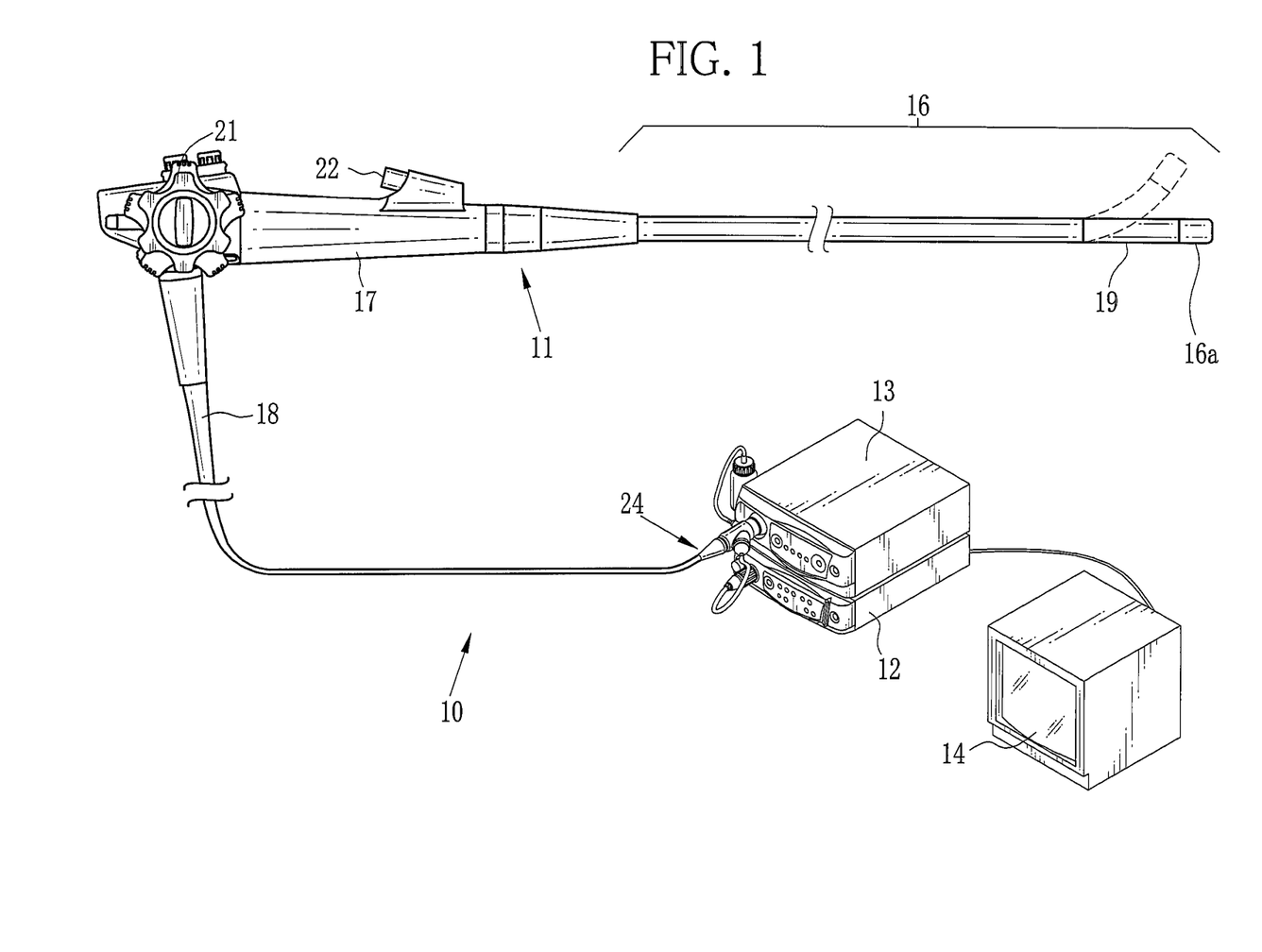
FIG. 1 is an external view of an electronic endoscope system according to a first embodiment of the present invention.

As shown in FIG. 1, in a first embodiment of the present invention, an electronic endoscope system 10 is provided with an electronic endoscope 11, a processing apparatus 12, a light source apparatus 13, and a monitor 14. The electronic endoscope 11 captures an image in a patient's body cavity. The processing apparatus 12 generates an image of a tissue site (an object of interest) in the body cavity based on a signal obtained with the image capture. The light source apparatus 13 supplies light for illuminating the body cavity. The monitor 14 displays the generated image. The electronic endoscope 11 is provided with a flexible insert section 16 to be inserted into the body cavity, a handling section 17 provided in the basal portion of the insert section 16, and a universal cord 18. The universal cord 18 connects the handling section 17, the processing apparatus 12, and the light source apparatus 13.

As is generally known, the insert section 16 has a bending portion 19 at its tip. The bending portion 19 has multiple joint pieces. Operating an angle knob 21 provided in the handling section 17 bends the bending portion 19 in horizontal and vertical directions. A distal portion 16a is provided at a distal end of the bending portion 19. The distal portion 16a incorporates an optical system used for the image capture of the body cavity. Bending the bending portion 19 directs the distal portion 16a to a desired direction.

A connector 24 is attached to one end of the universal cord 18 where the processing apparatus 12 and the light source apparatus 13 are to be connected. The connector 24 is a multiple-type connector composed of a communication connector and a light source connector. The electronic endoscope 11 is detachably connected to the processing apparatus 12 and the light source apparatus 13 via the connector 24.

Figure 2:
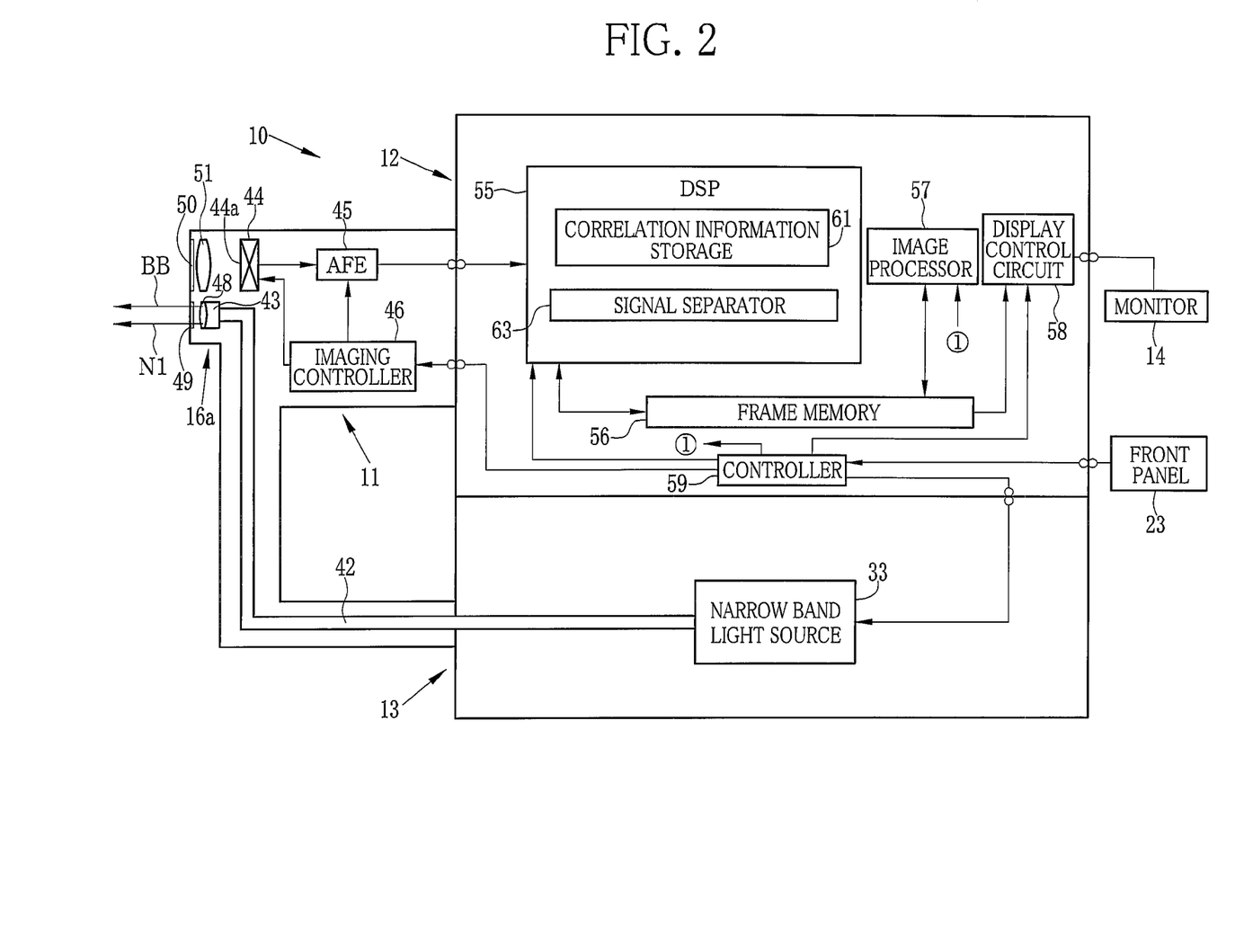
FIG. 2 is a block diagram showing an electric configuration of the electronic endoscope system.

As shown in FIG. 2, the light source apparatus 13 is provided with a narrow band light source 33, for example, a laser diode. The narrow band light source 33 generates narrow band light N1 having a wavelength of 440±10 nm, preferably, 445 nm. For example, a GaN semiconductor laser is used as the laser diode.

The electronic endoscope 11 is provided with a light guide 42, a fluorescent member 43, a CCD 44, an analog front-end (AFE) 45, and an imaging controller 46. The light guide 42 is, for example, a large core optical fiber or a bundle fiber. The light guide 42 is connected to the narrow band light source 33 in the light source apparatus 13. The light guide 42 guides the narrow band light N1 generated in the narrow band light source 33 to and through the electronic endoscope 11.

The fluorescent member 43 or phosphor device is attached to an exit end of the light guide 42. The narrow band light N1 guided through the light guide 42 excites the fluorescent member 43 to emit white broadband light BB in a wavelength range from 470 nm to 700 nm (that is, ranging from blue light to red light). A part of the narrow band light N1 passes through the fluorescent member 43. Thereby, the illumination light which is the combination of the broadband light BB and the narrow band light N1 is emitted from the fluorescent member 43. The combined illumination light is emitted to the tissue site in the body cavity via an illumination lens 48 and an illumination window 49. The illumination light reflected from the tissue site enters a focus lens 51 via an image capturing window 50 provided at the end surface of the distal portion 16a. The light emission device having the GaN semiconductor laser, the light guide 42, and the fluorescent member 43 is commercially available under the product name MicroWhite, for example.

Figure 3:
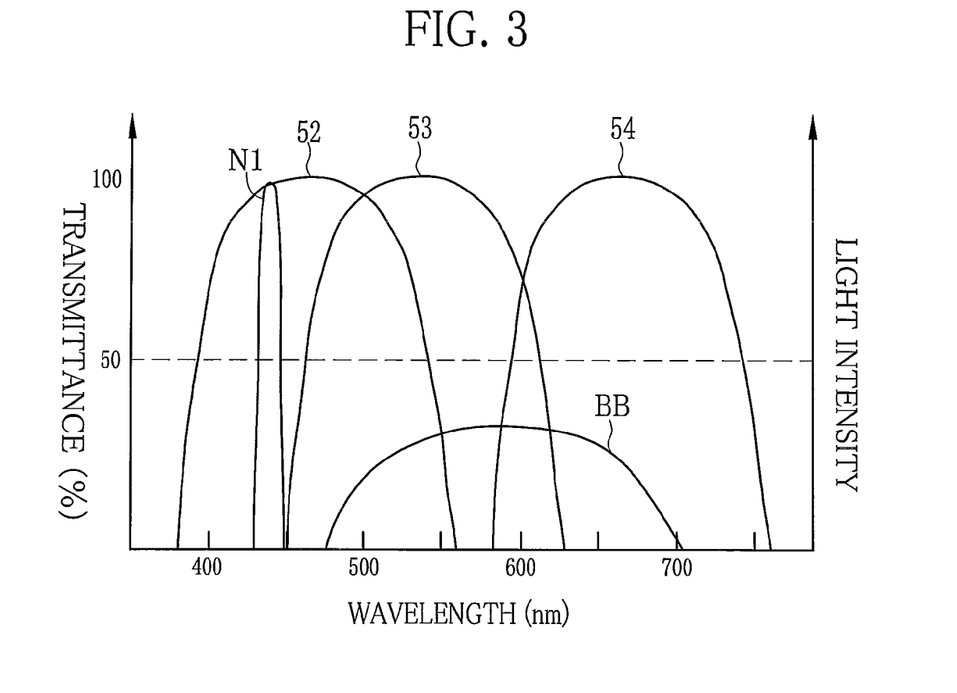
FIG. 3 is a graph showing spectral transmittances of red, green, blue filters, a wavelength range of narrow band light N1, and a wavelength range of broadband light BB.

The CCD 44 is a color CCD. On the imaging surface 44a, blue, green and red (B, G, and R) pixels are arranged in matrix. The B pixel is provided with a blue filter. The G pixel is provided with a green filter. The R pixel is provided with a red filter. As shown in FIG. 3, the blue filter, the green filter, and the red filter have spectral transmittances 52, 53, and 54, respectively. An imaging surface 44a of the CCD 44 receives the light from the focus lens 51. The CCD 44 photoelectrically converts the light into signal charge and accumulates the signal charge. The imaging controller 46 reads the accumulated signal charge of the B, G, and R pixels in time order and forms an image signal (CCD RAW) in which pixel signals of three colors (B, G, and R) are arranged. The imaging controller 46 sends the image signal to the AFE 45. An imaging section is composed of the focusing lens 51 and the CCD 41. The imaging controller 46 is a signal obtaining section.

In the CCD 44, the B pixel photoelectrically converts the blue light passing through the blue filter to output a blue color signal. The G pixel photoelectrically converts the green light passing through the green filter to output a green color signal. The R pixel photoelectrically converts the red light passing through the red filter to output a red color signal. The broadband light BB in a wavelength range of approximately from 470 nm to 700 nm enters the B pixel, the G pixel, and the R pixel through the blue filter, the green filter, and the red filter, respectively. Because all of the B, G, and R pixels have sensitivity to the broadband light BB, when only the broadband light BB enters the CCD 44, a B image signal (blue color signal), a G image signal (green color signal), and an R image signal (red color signal) are obtained. The B image signal represents a brightness value F1 of a blue (B) component of the broadband light BB. The G image signal has a brightness value F2 of a green (G) component of the broadband light BB. The R image signal has a brightness value F3 of a red (R) component of the broadband light BB. Hereafter, the B, G, and R image signals representing the brightness values F1, F2, and F3 are referred to as broadband image signals, respectively.

On the other hand, the narrow band light N1 is in a wavelength range of 440 nm±10 nm. The narrow band light N1 passes through the blue filter only, and then enters the B pixel. Accordingly, when only the narrow band light N1 enters the CCD 44, the B image signal having or representing a brightness value L1 of the narrow band light N1 is obtained. Hereafter, the B image signal having the brightness value L1 is referred to as narrow band image signal.

When the broadband light BB and the narrow band light N1 enter the CCD 44 simultaneously, the B pixel senses or detects both the narrow band light N1 and the B component of the broadband light BB. The G pixel does not sense the narrow band light N1, but the G component of the broadband light BB. The R pixel does not sense the narrow band light N1, but the R component of the broadband light BB. As shown in mathematical expressions below, the B pixel having sensitivity to the narrow band light outputs the B image signal (summed image signal) having the brightness value L1+F1, namely, the sum of the brightness value L1 of the narrow band light N1 and the brightness value F1 that is the B component of the broadband light BB. The G pixel not having the sensitivity to the narrow band light N1 outputs the G image signal that is the brightness value F2 of the G component of the broadband light BB (hereafter, a pixel not having the sensitivity to the narrow band light N1 is referred to as broadband light sensing pixel or non sensitivity pixel). The R pixel (broadband light sensing pixel) outputs the R image signal that is the brightness value F3 of the R component of the broadband light BB. Accordingly, the imaging section outputs a mixed image signal in which the broadband image signal and the narrow band image signal are mixed.

B image signal=brightness value L1+brightness value F1
G image signal=brightness value F2
R image signal=brightness value F3

The AFE 45 is composed of a correlated double sampling circuit (CDS), an automatic gain control circuit (AGC), and an analog/digital converter (A/D) (all not shown). The CDS performs correlated double sampling to the image signal from the CCD 44 to remove noise caused by the CCD 44. Then, the AGC amplifies the image signal. Thereafter, the A/D converts the image signal into a digital image signal (mixed image signal) having a predetermined number of bits and inputs the digital image signal to the processing apparatus 12.

The imaging controller 46 is connected to a controller 59 in the processing apparatus 12. The imaging controller 46 sends a drive signal to the CCD 44 when instructed by the controller 59. Based on the drive signal from the imaging controller 46, the CCD 44 outputs the image signal to the AFE 45 at a predetermined frame rate.

The processing apparatus 12 is provided with a front panel 23, a digital signal processor (DSP) 55, a frame memory 56, an image processor 57 and a display control circuit 58. The controller 59 controls each of the above sections. Inputting a control signal from the front panel 23 or the like controls the controller 59.

The DSP 55 receives the mixed image signal digitized in the AFE 45, and then writes the mixed image signal into the frame memory 56. The DSP 55 reads the mixed image signal from the frame memory 56, and then performs signal processing to the mixed image signal. The DSP 55 is provided with a correlation information storage 61 and a signal separator 63.

The correlation information storage 61 stores correlation information describing a correlation among the brightness value F1 of the B component of the broadband light BB, the brightness value F2 of the G component of the broadband light BB, and the brightness value F3 of the R component of the broadband light BB outputted from the B pixel, the G pixel, and the R pixel, respectively. The brightness values F1, F2, and F3 are obtained with the emission of only the broadband light BB (white light) to the tissue site in the digestive tract composed of esophagus, stomach, and intestine. The correlation information is obtained from analysis of a plurality of image data captured and stored for the diagnosis of the digestive tract.

Figure 4:
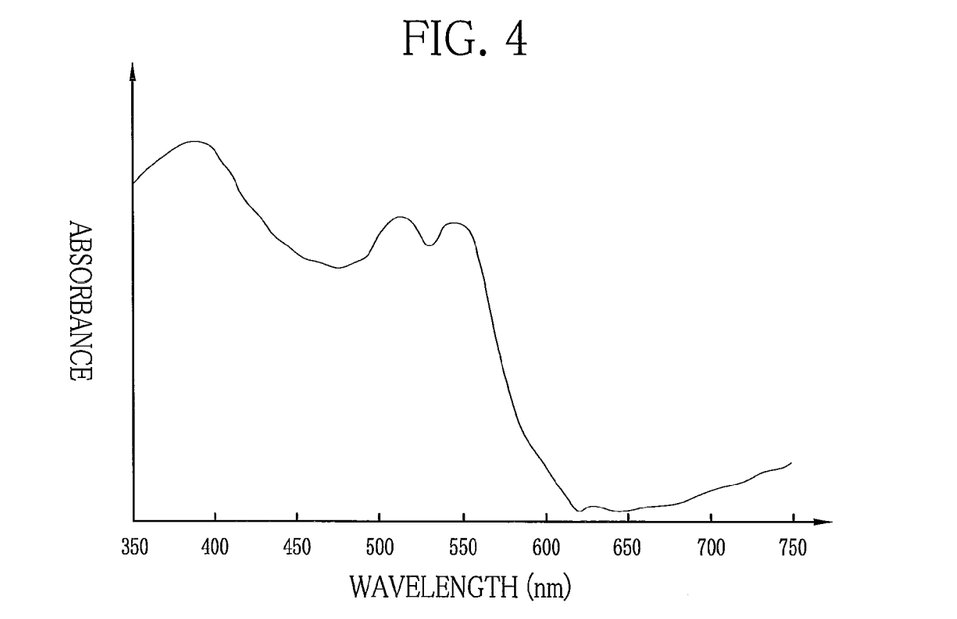
FIG. 4 is a graph showing absorbance of hemoglobin.
Figure 5:
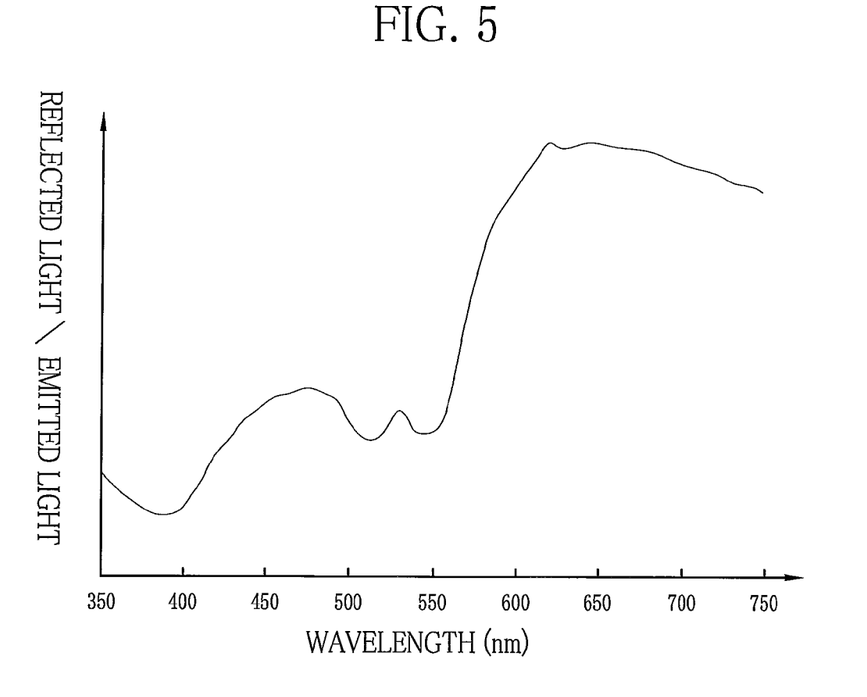
FIG. 5 is a graph showing reflectance spectrum of the tissue site when broadband light is emitted thereto.

As shown in FIG. 4, hemoglobin in blood has low absorbance in a wavelength range of red, and higher absorbance in wavelength ranges of blue and green compared to that of red. When the broadband light BB is emitted to the tissue site, a reflectance spectrum (see FIG. 5) of the tissue site is obtained. The reflectance spectrum shows a ratio of reflected light/emitted light for each wavelength, that is, the ratio of the intensity of the light reflected from the tissue site and received with the CCD 44 to the intensity of the light emitted. The reflectance spectrum describes that the color of the tissue site in the digestive tract mainly depends on the color of blood containing hemoglobin in the blood vessels.

Figure 6:
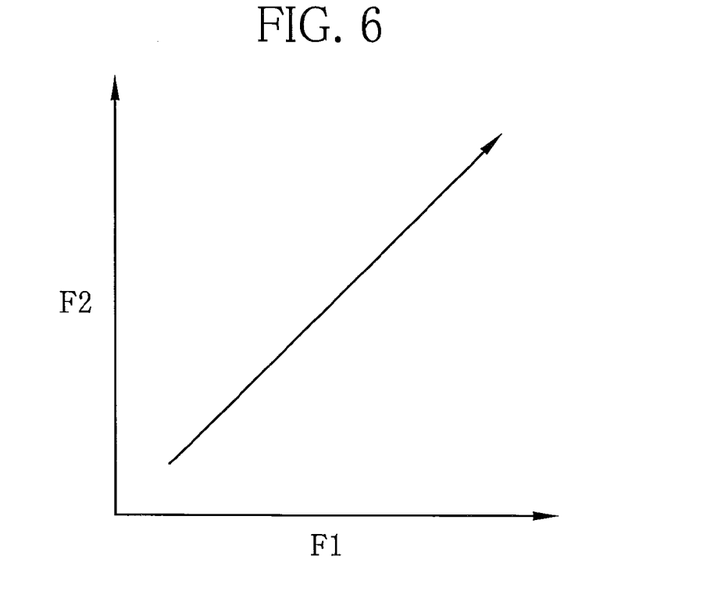
FIG. 6 is a graph showing a correlation between a brightness value F1 of a B component of the broadband light and a brightness value F2 of a G component of the broadband light.

Although the reflectance spectrum of the tissue site largely differs depending on the site of the digestive tract, the reflectance spectrum of the entire digestive tract mainly depends on the absorbance spectrum of hemoglobin. Accordingly, the reflectance spectral profile of the tissue site indicates correlations among the brightness values F1, F2, and F3 outputted from the B, G, and R pixels of the CCD 44 when only the broadband light BB is emitted. For example, as shown in FIG. 6, there is a positive correlation between the brightness value F1 and the brightness value F2 that the brightness value F2 increases as the brightness value F1 increases. The correlation between the brightness values F1 and F3, and the correlation between the brightness values F2 and F3 are similar to the above correlation between the brightness values F1 and F2. The correlation information storage 61 stores the above correlation information among the brightness values F1, F2, and F3 expressed by the following mathematical expressions.

$$F1 = \alpha \times F2 + \beta \quad (1)$$

$$F1 = \gamma \times F3 + \delta \quad (2)$$

$$F2 = \epsilon \times F3 + \eta \quad (3)$$

where each of $\alpha$, $\beta$, $\gamma$, $\delta$, $\epsilon$, and $\eta$ represents a constant, each of $\alpha$, $\gamma$, and $\epsilon$ is a positive number, and each of $\beta$, $\delta$, and $\eta$ is a bias value.

The signal separator 63 separates the mixed image signal into the broadband image signal and the narrow band image signal based on the correlation information stored in the correlation information storage 61. First, the signal separator 63 extracts the G image signal, outputted from the G pixel (the broadband light sensing pixel), from the mixed image signal. The G image signal represents the brightness value F2 of the G component of the broadband light BB. Next, the signal separator 63 substitutes the brightness value F2 into the mathematical expression (1) indicating the correlation between the brightness values F1 and F2. Thereby, the brightness value F1 of the B component of the broadband light BB contained in the B image signal outputted from the B pixel (the narrow band light sensing pixel) is obtained. Lastly, the brightness value F1 is subtracted from the B image signal to obtain the brightness value L1 of the narrow band light N1. Thus, the mixed image signal is separated into the broadband image signal representing the brightness value F1 of the B component of the broadband light BB, the broadband image signal representing the brightness value F2 of the G component of the broadband light BB, and the broadband image signal representing the brightness value F3 of the R component of the broadband light BB, and the narrow band image signal representing the brightness value L1 of the narrow band light N1.

Then, the DSP 55 performs the signal processing to the broadband image signals and the narrow band image signal. The signal processing includes white balance adjustment and gamma correction, for example.

Thereafter, the DSP 55 generates image data of the broadband image based on the broadband image signal and image data of the narrow band image based on the narrow band image signal. The generated image data is stored in the frame memory 56.

The image processor 57 performs image processing to the image data of the narrow band image. To be more specific, after a blood vessel region in the narrow band image is determined or identified, the image data of the blood vessel region is subjected to contrast processing to increase or reduce the contrast therein. The blood vessel region in the narrow band image is determined using a difference between the brightness value of the blood vessel region and the brightness value of the remaining region, for example. The narrow band image is obtained with the emission of the narrow band light N1 in the blue wavelength range having a low penetration depth. In the narrow band image, a blood vessel region located close to the surface (hereafter referred to as surface blood vessel region) is enhanced.

To further enhance the surface blood vessel region, the image processor 57 increases the contrast. To make the blood vessel region inconspicuous, on the other hand, the image processor 57 reduces the contrast. The contrast is adjusted appropriately depending on the region of interest and the purpose of diagnosis. The contrast processing makes the region of interest easily distinguishable. After the contrast processing, the narrow band image data is stored in the frame memory 56.

Figure 7:
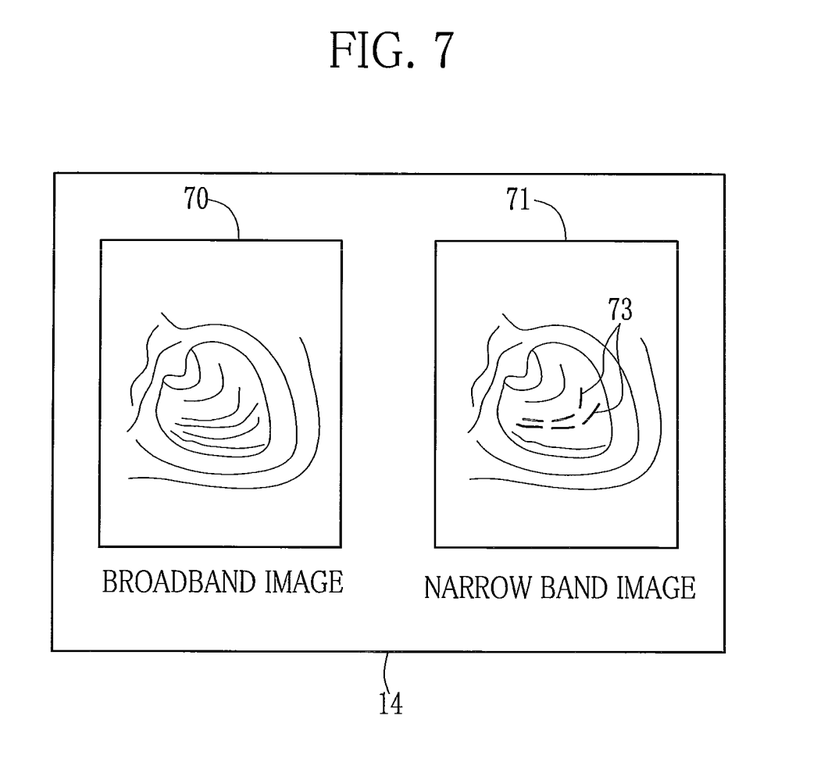
FIG. 7 shows a monitor on which a broadband image and a narrow band image are displayed together.

The display control circuit 58 converts the image data read from the frame memory 56 into an NTSC composite signal, for example. As shown in FIG. 7, a broadband image 70 and a narrow band image 71 are displayed side by side on the monitor 14.

Figure 8:
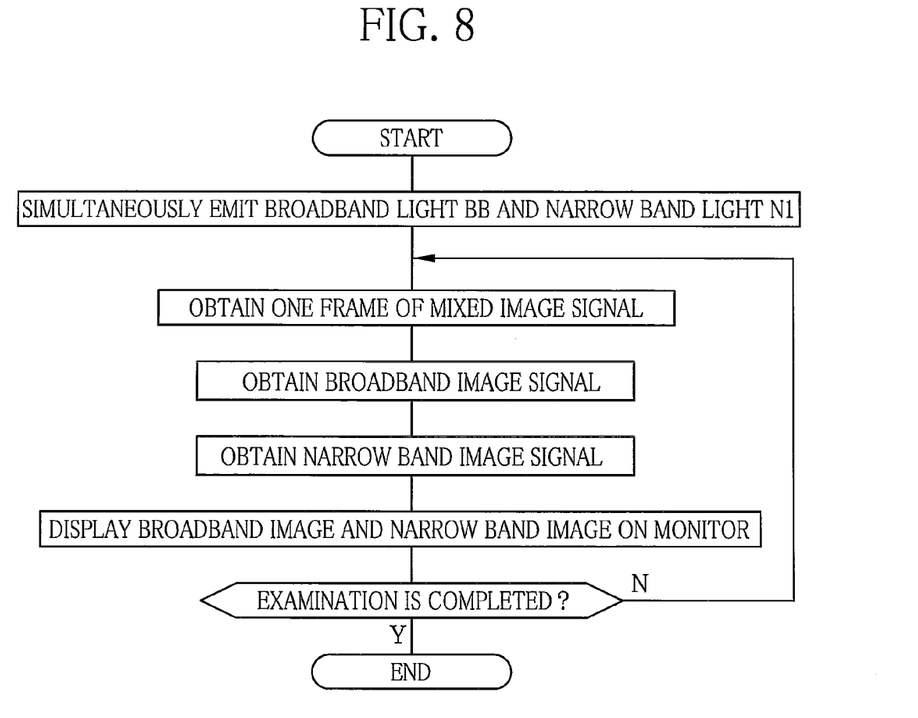
FIG. 8 is a flowchart showing steps of generating and displaying the broadband image and the narrow band image.

Next, referring to FIG. 8, an operation of the above configuration is described. To perform a digestive tract examination using the electronic endoscope system 10, the processing apparatus 12 and the light source apparatus 13 are turned on. Then the insert section 16 of the electronic endoscope 11 is inserted into a body cavity, specifically, the upper or lower digestive tract.

When the light source apparatus 13 is turned on, the narrow band light source 33 emits the narrow band light N1. The light guide 42 guides the narrow band light N1 to the fluorescent member 43. The fluorescent member 43 emits illumination light which is the combination of the broadband light BB excited by the narrow band light N1 and the narrow band light N1 passing through the fluorescent member 43. Thus, the broadband light BB and the narrow band light N1 are simultaneously emitted to the tissue site in the digestive tract through the illumination window 49.

The illumination light is reflected by the tissue site. The reflected light enters the imaging surface 44a of the CCD 44. The CCD 44 repeats imaging of the reflected light at a predetermined frame rate. One frame of the mixed image signal in which the broadband image signal and the narrow band image signal are mixed or combined is outputted per imaging operation. The DSP 55 obtains one frame of the mixed image signal through the AFE 45.

The signal separator 63 extracts G image signal of G pixel (broadband light sensing pixel) and B image signal of B pixel (narrow band light sensing pixel) from the mixed image signal. The G image signal is solely composed of the broadband image signal (the brightness value F2). The B image signal is the summed image signal of the broadband image signal (the brightness value F1) and the narrow band image signal (the brightness value L1). Based on the G image signal (the brightness value F2) and the correlation information, indicated by the above mathematical expression (1), stored in the correlation information storage 61, the signal separator 63 obtains the broadband image signal (the brightness value F1) contained in the B image signal of the B pixel. Based on the equation "B image signal=brightness value F1+brightness value L1", the broadband image signal (the brightness value F1) is subtracted from the B image signal to obtain the narrow band image signal (the brightness value L1).

Thus, the mixed image signal is separated into the broadband image signal representing the brightness value F1 of the B component of the broadband light BB, the broadband image signal representing the brightness value F2 of the G component of the broadband light BB, and the broadband image signal representing the brightness value F3 of the R component of the broadband light BB, and the narrow band image signal representing the brightness value L1 of the narrow band light N1. The image processor 57 performs contrast processing to the narrow band image signal to adjust contrast of the surface blood vessel region. The display control circuit 58 generates the broadband image 70 and a narrow band image 71 based on the separated broadband image signal and the separated narrow band image signal, respectively. As shown in FIG. 7, the broadband image 70 and the narrow band image 71 are displayed side by side on the monitor 14. The above described steps are repeated until the examination is completed.

As described above, the combined illumination light of the broadband light BB and the narrow band light N1 is emitted to the tissue site to obtain one frame of the mixed image signal. The mixed image signal is separated into the broadband image signals and the narrow band image signal to generate and display the broadband image 70 and the narrow band image 71. Conventionally, the broadband image signal and the narrow band image signal are obtained from two frames of image signals captured at different timing, respectively. This causes the misregistration between the broadband image and the narrow band image due to the body motion of the patient and the motion of the insert section.

The present invention, on the other hand, the broadband image signal and the narrow band image signal are obtained at the same timing from one frame of the mixed image signal. As a result, the misregistration is prevented. In the present invention, the mixed image signal is separated into the broadband image signals and the narrow band image signal based on the correlation information among the brightness values of the B, G, and R pixels obtained with the emission of only the broadband light BB. Thus, the present invention does not require an expensive device such an acousto-optic filter, to reduce cost.

In the first embodiment described as an example, the G pixel is the broadband light sensing pixel, and the broadband image signal (the brightness value F2) of the G pixel is used to obtain the broadband image signal (the brightness value F1) of the B pixel (the narrow band light sensing pixel). Instead, the broadband image signal (the brightness value F3) of the R pixel (the other broadband light sensing pixel) may be used to obtain the broadband image signal (the brightness value F1) of the B pixel.

In the first embodiment, the narrow band light N1 in the wavelength range of 440±10 nm is emitted. The wavelength range of the narrow band light N1 is not limited to the above as long as the narrow band light N1 is sensed or detected only by the B pixel. For example, the narrow band light N2 may be in a wavelength range of 400±10 nm. In the above example, the narrow band light sensing pixel is the B pixel. Alternatively, the narrow band light sensed by one of the G pixel and the R pixel may be used. In this case, the narrow band light sensing pixel is one of the G pixel and the R pixel.

As described above, the light penetrates deeper into the tissue site as its wavelength increases, namely, the blue light, the green light, and the red light increase in penetration depth in this order. When the narrow band light sensed by the G pixel or the R pixel is used, the blood vessel region enhanced in the narrow band image is located deeper than that obtained with the narrow band light sensed by the B pixel. Thus, the wavelength range of the narrow band light is selected or determined based on the depth of a region of interest (in this case the blood vessel region). Two or more narrow band light sources each of which is capable of emitting the narrow band light in a different wavelength range may be provided to change the wavelength range of the narrow band light.

In the first embodiment described as an example, there are one narrow band light sensing pixel and two broadband light sensing pixels. Alternatively, there may be two narrow band light sensing pixels and one broadband light sensing pixel. In this case, for example, as shown in the second embodiment shown in FIG. 9, the narrow band light N3 in the wavelength range of 470±10 nm is used. The wavelength range of the light sensed by the B pixel and the wavelength range of the light sensed by the G pixel are partly overlapped with each other, and the wavelength range of 470±10 nm is within the overlapped wavelength range. Accordingly, the narrow band light N3 is sensed by the B pixel and the G pixel.

Figure 9:
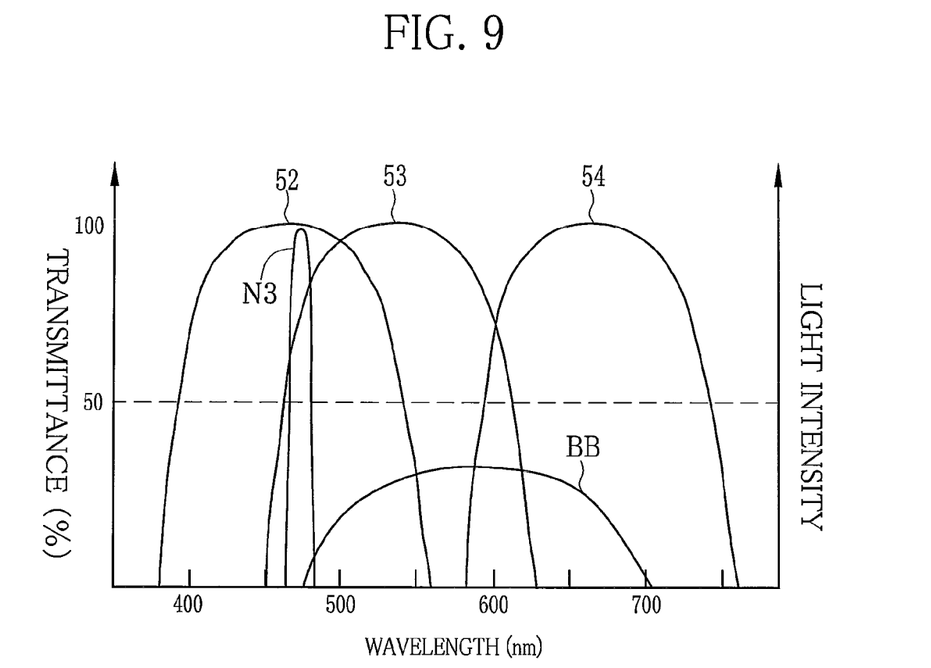
FIG. 9 is a graph showing the spectral transmittances of the red, green, and blue filters, a wavelength range of narrow band light N3, and the wavelength range of the broadband light BB.

When the broadband light BB and the narrow band light N3 are simultaneously emitted, the CCD 44 outputs a mixed image signal in which the broadband image signals representing the brightness values of the broadband light BB and the narrow band image signals representing the brightness values of the narrow band light N3 are mixed or combined. As shown in the equations below, in this mixed image signal, the B image signal represents the sum (summed brightness value) of the brightness value F1 (B component of the broadband light BB) and the brightness value L1 (B component of the narrow band light N3). The G image signal represents the sum (summed brightness value) of the brightness value F2 (G component of the broadband light BB) and the brightness value L2 (G component of the narrow band light N3). The R image signal represents the brightness value F3 of the broadband light.

B image signal=brightness value L1+brightness value F1
G image signal=brightness value L2+brightness value F2

R image signal=brightness value F3

In the second embodiment, the only broadband light sensing pixel is the R pixel. Based on the R image signal (the brightness value F3) solely composed of the broadband image signal, the signal separator 63 separates each of the B image signal, outputted from the B pixel (narrow band light sensing pixel), and the G image signal, outputted from the G pixel (narrow band light sensing pixel), into the broadband image signal and the narrow band image signal. To separate the broadband image signal and the narrow band image signal, first, the signal separator 63 extracts each of the B, G, and R image signals from the mixed image signal. The signal separator 63 reads the mathematical expression (2) indicating the correlation between the brightness values F1 and F3 from the correlation information storage 61. The R image signal (the brightness value F3) is substituted into the mathematical expression (2) to obtain the broadband image signal (the brightness value F1, that is, the B component of the broadband light BB) contained in the B image signal.

To obtain the broadband image signal (the brightness value F2, that is, the G color component of the broadband light) contained in the G image signal, the R image signal (the brightness value F3) is substituted into the mathematical expression (3) indicating the correlation between the brightness values F2 and F3. Then, the broadband image signal (the brightness value F1) is subtracted from the B image signal to obtain the narrow band image signal (the brightness value L1), and the broadband image signal (the brightness value F2) is subtracted from the G image signal to obtain the narrow band image signal (the brightness value L2). Thus, the mixed image signal is separated into the broadband image signal representing the brightness value F1 of the B component of the broadband light BB, the broadband image signal representing the brightness value F2 of the G component of the broadband light BB, the broadband image signal representing the brightness value F3 of the R component of the broadband light BB, the narrow band image signal representing the brightness value L1 of the B component of the narrow band light N1, and the narrow band image signal representing the brightness value L2 of the G component of the narrow band light N1.

In the above second embodiment described as an example, two pixels, namely, the B pixel and the G pixel are the narrow band light sensing pixels, and the R pixel is the broadband light sensing pixel. Alternatively, the G pixel and the R pixel may be the narrow band light sensing pixels. In this case, the narrow band light has a wavelength range sensed by the G pixel and the R pixel.

In the above embodiments described as examples, the broadband light and the narrow band light are simultaneously emitted into the body cavity, and the broadband image and the narrow band image are displayed side by side. Alternatively or in addition, one of the broadband image and the narrow band image may be displayed selectively. In the case where only the broadband image is displayed, the broadband image may be generated based on the mixed image signal without the signal separation.

In the above embodiments described as examples, only the narrow band light source is provided as the light source. The narrow band light (excitation light) from the narrow band light source excites the fluorescent member to generate the broadband light BB. In addition to the narrow band light source, a broadband light source designed specifically for generating the broadband light BB may be provided.

The present invention can be applicable to the electronic endoscope having the insert section, and also to a capsule-type electronic endoscope having an image sensor such as a CCD incorporated in a capsule, and an electronic endoscope for imaging of a body cavity other than the digestive tract, for example, respiratory tract.

Various changes and modifications are possible in the present invention and may be understood to be within the present invention.

What is claimed is:

1. An electronic endoscope system comprising:
   an emission section for emitting white broadband light and narrow band light to a tissue site in a body cavity, the tissue site including a blood vessel;
   an imaging section in which a blue pixel, a green pixel, and a red pixel are arranged, the broadband light being sensed by the three color pixels, and the narrow band light being sensed by only one or two of the three color pixels;
   a signal obtaining section for obtaining a mixed image signal during emission of the broadband light and the narrow band light, the mixed image signal including a first color signal which is outputted from the pixel having sensitivity to the narrow band light and has a sum of a brightness value of the broadband light and a brightness value of the narrow band light, and a second color signal which is outputted from the pixel not having sensitivity to the narrow band light and has only a brightness value of the broadband light;
   a correlation information storage for storing correlation information between a brightness value of the pixel having sensitivity to the narrow band light and a brightness value of the pixel not having sensitivity to the narrow band light when only the broadband light is emitted; and
   a signal separator configured to calculate a brightness value of the broadband light contained in the first color signal from a brightness value of the broadband light contained in the second color signal and the correlation information, and subtract the calculated brightness value from the first color signal to obtain a brightness value of the narrow band light contained in the first color signal.

2. The electronic endoscope system of claim 1, further including an electronic endoscope, a processing apparatus connected to the electronic endoscope, and a light source apparatus connected to the electronic endoscope;
   and wherein the electronic endoscope is provided with the emission section, the signal obtaining section, and the imaging section;
   and wherein the processing apparatus is provided with the correlation information storage and the signal separator;
   and wherein the light source apparatus is provided with a light source for generating the narrow band light, and a part of the narrow band light passes through a fluorescent member provided in the endoscope, and the fluorescent member converting a remainder of the narrow band light into the broadband light.

3. The electronic endoscope system of claim 1, wherein the pixel sensing the narrow band light is the blue pixel.

4. The electronic endoscope system of claim 3, wherein the narrow band light is in a wavelength range of 440±10 nm or 400±10 nm.

5. The electronic endoscope system of claim 1, wherein the pixel sensing the narrow band light is the blue pixel and the green pixel.

6. The electronic endoscope system of claim 5, wherein the narrow band light is in a wavelength range of 470±10 nm.

7. The electronic endoscope system of claim 1, further including a monitor for displaying a broadband image based on a broadband image signal and a narrow band image based on the narrow band image signal, the broadband image signal representing a brightness value of each color component of the broadband light, and the narrow band image signal representing a brightness value of each color component of the narrow band light.

8. A processing apparatus connected to an electronic endoscope, the electronic endoscope having an imaging section in which a blue pixel, a green pixel, and a red pixel are arranged, the imaging section capturing an image of a tissue site in a body cavity during emission of white broadband light and narrow band light, the tissue site including a blood vessel, the broadband light being sensed by the three color pixels, and the narrow band light being sensed by only one or two of the three color pixels, the processing apparatus comprising:
  a signal obtaining section for obtaining a mixed image signal during the emission of the broadband light and the narrow band light, the mixed image signal including a first color signal which is outputted from the pixel having sensitivity to the narrow band light and has a sum of a brightness value of the broadband light and a brightness value of the narrow band light, and a second color signal which is outputted from the pixel not having sensitivity to the narrow band light and has only a brightness value of the broadband light;
  a correlation information storage for storing correlation information between a brightness value of the pixel having sensitivity to the narrow band light and a brightness value of the pixel not having sensitivity to the narrow band light when only the broadband light is emitted; and
  a signal separator configured to calculate a brightness value of the broadband light contained in the first color signal from a brightness value of the broadband light contained in the second color signal and the correlation information, and subtract the calculated brightness value from the first color signal to obtain a brightness value of the narrow band light contained in the first color signal.

9. A signal separation method for separating an image signal of an electronic endoscope, the electronic endoscope having an imaging section in which a blue pixel, a green pixel, and a red pixel are arranged, the signal separation method comprising the steps of;
  emitting white broadband light and narrow band light to a tissue site in a body cavity, the tissue site including a blood vessel, the broadband light being sensed by the three color pixels, and the narrow band light being sensed by only one or two of the three color pixels;
  capturing an image of the tissue site with the imaging section during emission of the broadband light and the narrow band light and obtaining a mixed image signal, the mixed image signal including a first color signal which is outputted from the pixel having sensitivity to the narrow band light and has a sum of a brightness value of the broadband light and a brightness value of the narrow band light, and a second color signal which is outputted form the pixel not having sensitivity to the narrow band light and has only a brightness value of the broadband light;
  reading correlation information from a correlation information storage, the correlation information representing a correlation between a brightness value of the pixel having sensitivity to the narrow band light and a brightness value of the pixel not having sensitivity to the narrow band light when only the broadband light is emitted; and
  calculating a brightness value of the broadband light contained in the first color signal from a brightness value of the broadband light contained in the second color signal and the correlation information, and subtracting the calculated brightness value from the first color signal to obtain a brightness value of the narrow band light contained in the, first color signal.

* * * * *